United States Patent
Viswanathan

(10) Patent No.: US 7,815,580 B2
(45) Date of Patent: Oct. 19, 2010

(54) MAGNETIC GUIDEWIRE FOR LESION CROSSING

(75) Inventor: Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1047 days.

(21) Appl. No.: 11/220,383

(22) Filed: Sep. 6, 2005

(65) Prior Publication Data

US 2006/0079812 A1    Apr. 13, 2006

Related U.S. Application Data

(60) Provisional application No. 60/607,614, filed on Sep. 7, 2004.

(51) Int. Cl.
- *A61M 25/092* (2006.01)
- *A61M 25/09* (2006.01)
- *A61M 25/00* (2006.01)
- *A61M 5/00* (2006.01)

(52) U.S. Cl. .................................... 600/585
(58) Field of Classification Search ............ 600/585
See application file for complete search history.

(56) References Cited

U.S. PATENT DOCUMENTS

| | | | |
|---|---|---|---|
| 5,460,187 A * | 10/1995 | Daigle et al. ............ | 600/585 |
| 5,931,818 A * | 8/1999 | Werp et al. ............. | 604/270 |
| 6,401,723 B1 * | 6/2002 | Garibaldi et al. ........ | 128/899 |
| 6,505,062 B1 * | 1/2003 | Ritter et al. ............ | 600/407 |
| 2004/0102719 A1 * | 5/2004 | Keith et al. ............ | 600/585 |
| 2004/0116833 A1 * | 6/2004 | Kato et al. ............. | 600/585 |

FOREIGN PATENT DOCUMENTS

JP        63262160 A    * 10/1988

* cited by examiner

*Primary Examiner*—Max Hindenburg
*Assistant Examiner*—Emily M Lloyd
(74) *Attorney, Agent, or Firm*—Harness, Dickey & Pierce, P.L.C.

(57) ABSTRACT

The invented guidewire relates to improvements in a magnetically navigable medical guidewire to enable passage through an occluded or partially occluded vessel. The guidewire comprises an elongate wire having a proximal end and a distal end, wherein the distal end further comprises a magnetically responsive element and a helical thread formed on the tip. The distal end of the guidewire may be preferably aligned substantially in the direction of an applied magnetic field, after which the proximal end of the guidewire may be torqued to rotate the threaded tip while remaining aligned with the applied magnetic field and cause the tip to screw through the blockage in the occluded vessel.

39 Claims, 2 Drawing Sheets

MAGNETIC GUIDEWIRE FOR LESION CROSSING

CROSS-REFERENCE TO RELATED APPLICATIONS

This application claims benefit of U.S. Provisional Patent Application Ser. No. 60/607,614 filed Sep. 7, 2004, the entire disclosure of which is incorporated by reference.

BACKGROUND OF THE INVENTION

This invention relates to guidewires for facilitating the navigation of medical devices through the vasculature, and in particular to guidewires adapted for passing occlusions in the vasculature.

Navigation of a conventional guidewire involves rotating or applying a torque to the proximal end of the guidewire repeatedly to rotate the distal tip while the wire is pushed. This action is repeated until, by trial and error, the tip enters the desired vessel branch. In navigating guidewires in the vasculature of the body, an important criterion is that the tip of the guidewire be flexible enough to negotiate the sharp turns that are necessary to reach the target area for medical intervention. At the same time, in some medical procedures, particularly in coronary occlusion, flexibility can become a disadvantage when the tip is at the position of a total occlusion. Physicians presently attempt to manipulate the proximal end of the guidewire in a way to punch through such an occlusion. Typically, the flexible guidewire will buckle and fail to provide the passage through the occlusion, which would be necessary in order to implant a stent. Furthermore, after the guidewire has made several bends, the guidewire becomes increasingly difficult to control, requiring repeated attempts to enter a desired vessel branch or gain access through an occlusion. This trial and error method can frustrate the physician and cause additional wall contact and potential trauma.

To address these and other difficulties, magnetically navigable guidewires have been developed which can be controlled with the application of an external magnetic field. An example of magnetically navigable guidewire is disclosed in Werp et al., U.S. Pat. No. 5,931,818 (incorporated in its entirety herein by reference). The user can advance the magnetically navigable guide wire into vessels with little or no contact between the end of the wire and the vessel wall. When the distal end of the guidewire is adjacent the vessel of interest, the user operates a magnetic system to apply a magnetic field (preferably with the aid of a computerized user interface) to deflect the wire tip to align with the vessel side branch. The magnet system can be made sufficiently accurate to direct the distal end of the guidewire into the brach on the first effort, eliminating the trial and error of manually operated guidewires and thereby reducing or eliminating trauma to the vessel wall. The deflection of the guidewire tip is controlled by the external magnets in magnetic navigation, and in normal use, the physician does not need to apply torque to the guidewire. However, while prior magnetically navigable guidewires are very effective at navigating through tortuous paths in the vasculature of a subject, these guidewires do not address the challenge of crossing or pushing through an occluded or partially occluded vessel in the vasculature of a subject's body.

SUMMARY OF THE INVENTION

The present invention relates to improvements in the construction of magnetically navigable medical guidewires to facilitate passage through an occulated or partially occulated vessel. Generally, a preferred embodiment of a guidewire constructed in accordance with the principles of this invention comprises an elongate corewire having a proximal end and a distal end. A coil may surround at least the distal portion of the corewire. The distal end further comprises a magnetically responsive element and a helical thread formed on the tip. This magnetically responsive element preferably comprises a permanent magnetic material, but may alternatively comprise a permeable magnetic material. The magnetically responsive element is enclosed in a radiopaque sleeve at the distal end of the guidewire. Attached or integral to the sleeve, is a helical thread formed in the tip of the distal end of the guidewire. The guide wire is configured so that the distal end of the guidewire can be preferably oriented in the direction of an applied magnetic field. Once it is magnetically oriented, the proximal end of the guidewire may be torqued to rotate the threaded tip aligned with the field and cause the tip to screw through a blockage in an occluded or partially occluded vessel.

DETAILED DESCRIPTION OF THE INVENTION

Figure 1:
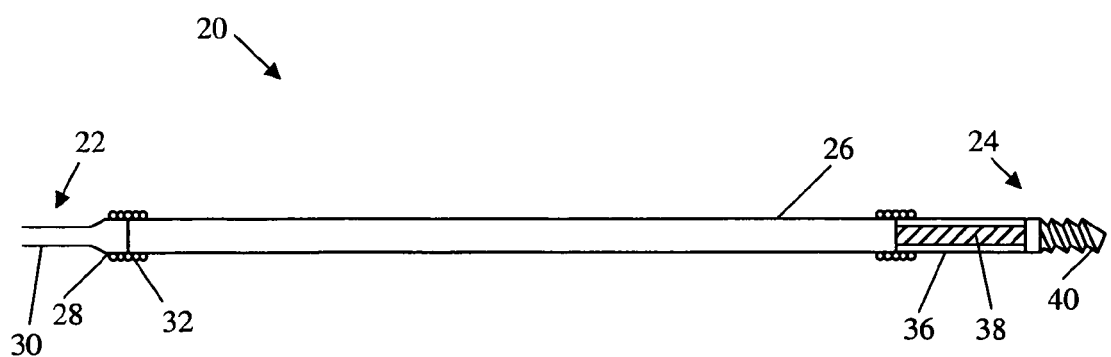
FIG. 1 is a side elevation view of a preferred embodiment guidewire constructed according to the principles of this invention.

A first preferred embodiment of a magnetically navigable medical guidewire is indicated generally as 20 in FIG. 1. The guidewire 20 has a proximal end 22 and a distal end 24 and comprises a flexible core wire 26 extending from the proximal end substantially to the distal end. The core wire 26 can be made of Nitinol or other suitable material. As shown in FIG. 1, the proximal end 22 of the guidewire 20 includes a conventional connector 28 having a proximal landing 30, to which a core wire 26 is attached. The attachment of the core wire 26 is preferably done by a coil 34 extending over the core wire 26 and the proximal landing 30. The distal end of the core wire 26 is attached in the same manner to a metallic cylinder or sleeve 36.

The cylinder or sleeve 36 may be made of, or at least plated with a radiopaque material so that the distal end of the guidewire 20 can be seen in x-ray imaging. The sleeve 36 is preferably made of gold, a gold alloy, or other biocompatible material. Disposed within a hollow section of the sleeve 36 is a magnetically responsive element 38, which may alternatively be embedded within the sleeve 36. The magnetically responsive element 38, which can be made of a permanent magnetic material or a permeable magnetic material, is disposed inside the sleeve 36. The magnetically responsive element 38 is of sufficient size and shape to cause the distal end portion of the guidewire 20 to align in a selected direction with a magnetic field applied from an external source magnet. Suitable permanent magnetic materials include neodymium-iron-boron (Nd—Fe—B). Suitable permeable magnetic materials include magnetic stainless steel, such as a 303 or 304 stainless steel, or other alloys such as Hiperco. The size and material of the magnetically responsive element 38 are selected so that the distal end portion of the guide wire can be reoriented by the application of a magnetic field of no more than about 0.20 Tesla. In the preferred embodiment, the length of the magnetically responsive element 38 is preferably about 2.2 millimeter, but may alternatively be any length in the range of 0.5 to 5 millimeters.

In the first preferred embodiment, the distal end of the sleeve 36 is solid and has an external helical thread 40 formed in the tip of the sleeve. Alternatively, a solid section 40A may be mounted on the distal end of the sleeve 36 and the ends of the sleeve and section 40A are secured to each other, such as by welding. The helical thread 40 may be formed by thread rolling, chasing, etching or other suitable process. In the preferred embodiment, the helical thread 40 may comprise one to ten complete thread turns over a predetermined length in the range of 0.5 to 4 millimeters, and preferably has three to four turns over a length of about 2.2 millimeters. By way of example only, and without limiting the invention the guidewire 20 of the preferred embodiment has a total length of about 180 cm.

The guidewire 20 is sufficiently stiff that it can be advanced in the selected direction by pushing the proximal end of the guidewire 20, yet flexible enough that the guidewire can be deflected by an applied magnetic field to gain entry to a vessel branch. Guidewire deflection can be measured by holding the wire at a set distance proximal to the tip such as 1 cm, and applying a magnetic field of known magnitude, H, at varying angles to the tip until the maximum tip deflection is observed. For example, in the Stereotaxis Niobe™ magnetic navigation system, an external field of 0.08 Tesla can be applied within the subject in any direction. The maximum deflection angle of the guidewire in a 0.08 Tesla field is thus one way to characterize the guidewire performance in the Niobe™ magnetic navigation system. The inventors have determined that in most circumstances a minimum tip deflection of about 30 degrees is desired for navigation of the guidewire according to the principles of the present invention.

In operation, the distal tip of the guidewire 20 in the presence of an applied magnetic field will tend to align with the field direction to the extent allowed by the flexibility of the guidewire. When the distal end has been deflected to a desired orientation, the proximal end 22 of the guidewire 20 is torqued or rotated about its longitudinal axis, to cause the distal end 24 of the guidewire to rotate or spin on an axis substantially in alignment with the field direction. Because of the tendency of the device tip to stay aligned with the field, rotating the proximal end of the wire about its axis will cause the distal tip to execute a similar rotation, while maintaining its alignment with the field. This property of "twisting in place" is a direct consequence of magnetic actuation, and is a significant advantage over conventional guidewires in which rotation of the tip is not so constrained. The helical thread 40 on the tip of the guidewire distal end 24 will accordingly spin or rotate about the longitudinal axis of the distal end 24 held in a substantially fixed alignment by the external magnetic field. By gently pushing on the proximal end 22 while rotating the guidewire 20, the distal tip 24 can screw or drill its way through an occluded vessel. The rotation may be produced either manually or with the use of a motor or suitable mechanism.

Figure 2:
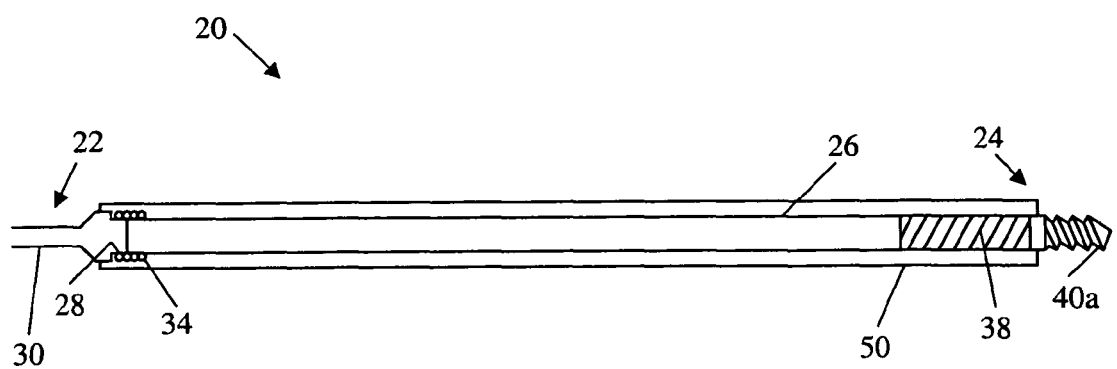
FIG. 2 is a side elevation view of an alternate construction of the preferred embodiment of a guidewire according to the principles of this invention.

An alternate construction of a preferred embodiment of a guidewire, in accordance with the principles of this invention, is indicated as 20' in FIG. 2. Guidewire 20' is similar in construction go guidewire 20, and corresponding reference numerals indicate corresponding parts throughout the several views of the drawings. The guidewire 20' has a proximal end 22 and a distal end 24. As also described above, the alternate construction guidewire 20' comprises a flexible core wire 26 extending from the proximal end substantially to the distal end. The proximal end 22 of the guidewire 20 includes a conventional connector 28 having a proximal landing 30, to which a core wire 26 is attached. The core wire 26 can be made of Nitinol or other suitable material, and may further comprise a wound coil 34 over the length of the core wire 26. The distal end of the core wire 26 attaches to a magnetically responsive element 38 that is preferably disposed within a metallic cup or encapsulated by a metallic coating, of a gold alloy or other suitable material. The core wire 26 and the encapsulated magnetically responsive element 38 are surrounded or covered by a flexible tube or jacket 50, made of a polymer or metal. The flexible tube 50 connects to a proximal landing 30 of a connector 28 on the proximal end 22 of the guidewire, and to a metallic distal tip 40a at the distal end 24 of the guidewire. The connection of the flexible tube 50 may be obtained by laser welding, adhesive bonding, or other suitable joining process. The metallic distal tip 40a comprises a helical thread as described above, and is preferably made of gold, a gold alloy, or other biocompatible material. By way of example only, and without limiting the invention the guidewire of the preferred embodiment has a total length of about 180 cm.

The above-described embodiments are intended to be illustrative only. For example, the mechanical pushing force applied to the proximal end of the guidewire may also be provided by using a motor that is controlled by a surgeon. Likewise, more than one magnetically responsive element could be incorporated in the guidewire, and at least one magnetically responsive element could be mechanically flexible and could be made of a material of high magnetic permeability. Some or all of the threaded elements could also be made of a magnetic material. There are also numerous types of magnetic surgery procedures for which the guidewire described and the method of controlling the guidewire are important. The invention can be readily adapted so that a surgeon, under guidance from an imaging system, uses the magnetic system to negotiate otherwise difficult turns and movements of the surgical device and to gain passage through an occulated vessel. It will also be recognized that many of the inventive methods and apparatuses may be used in conjunction with any coil in a non-resonant circuit that applies a magnetic force on a suspended or embedded object that is magnetically moveable. Many other modifications falling within the spirit of the invention will be apparent to those skilled in the art. Therefore, the scope of the invention should be determined by reference to the claims below and the full range of equivalents in accordance with applicable law.

What is claimed is:

1. An improved magnetically navigable medical guidewire having a proximal end and a distal end, and incorporating at least one magnetically responsive element, the improvement comprising:

a magnetically responsive element disposed within the distal tip of the guidewire, wherein the magnetically responsive element is of a size and shape sufficient to cause the distal end of the guide wire to stay aligned with the direction of a magnetic field while a torque is applied to the guide wire to rotate the guide wire, such that the distal tip rotates while maintaining its alignment with the field; and a threaded tip section at the distal tip of the guidewire, wherein the threaded tip comprises a helical thread on the external surface of the distal tip that forms at least one complete thread turn over a predetermined thread length.

2. The improved magnetically navigable medical guidewire of claim 1, wherein the threaded tip comprises a number of complete thread turns in the range of one to ten complete turns over a predetermined length of 0.5 to 4.0 millimeters.

3. The improved magnetically navigable medical guidewire of claim 2, wherein the threaded tip preferably comprises three to four complete thread turns over a predetermined length of about 2.2 millimeters.

4. The improved magnetically navigable medical guidewire of claim 3, wherein the threaded tip is made of gold or a gold alloy.

5. The improved magnetically navigable medical guidewire of claim 1, wherein the at least one magnetically responsive element has a length in the range of 0.5 to 5 millimeters.

6. The improved magnetically navigable medical guidewire of claim 5, wherein the at least one magnetically responsive element is made of neodymium-iron boron.

7. The improved magnetically navigable medical guidewire of claim 5, wherein the at least one magnetically responsive element is made of a material of high magnetic permeability.

8. The improved magnetically navigable medical guidewire of claim 1, wherein the at least one magnetically responsive element is responsively oriented in a selected direction by a magnetic navigation system through the interaction of magnetic fields associated with the magnetic member and at least one external source magnet outside the subject body.

9. The improved magnetically navigable medical guidewire of claim 8, wherein the tip of the guidewire is capable of being deflected a minimum of 30 degrees over a length of 1 cm measured proximally from the tip when subjected to a suitably oriented magnetic field of magnitude at least 0.06 Tesla.

10. A magnetically navigable medical guidewire, comprising:
    an elongate wire having a proximal end, and a distal end;
    a hollow cylindrical member disposed on the distal end of the elongate wire;
    a magnetically responsive element disposed within said hollow cylinder, wherein the magnetically responsive element is of a size and shape sufficient to cause the distal end of the guide wire to stay aligned with the direction of a magnetic field while a torque is applied to the guide wire to rotate the guide wire, such that the distal tip rotates while maintaining its alignment with the field; and
    a helical-threaded end forming an external thread on the outer surface of the distal end of the cylinder so as to seal the magnetically responsive element inside the hollow cylinder, wherein the helical thread comprises at least one complete thread turn over a predetermined thread length.

11. The magnetically navigable medical guidewire of claim 10, wherein the magnetically responsive element is encapsulated by the distal end of the elongate wire, the hollow cylindrical member and the threaded end.

12. The magnetically navigable medical guidewire of claim 10, wherein the threaded end comprises a number of complete thread turns in the range of one to ten complete turns over a predetermined length of 0.5 to 4.0 millimeters.

13. The magnetically navigable medical guidewire of claim 12, wherein the threaded end preferably comprises three to four complete thread turns over a predetermined length of about 2.2 millimeters.

14. The magnetically navigable medical guidewire of claim 13, wherein the cylindrical member and threaded end is made of gold or a gold alloy.

15. The magnetically navigable medical guidewire of claim 10, wherein the magnetically responsive element has a length in the range of 0.5 to 5 millimeters.

16. The magnetically navigable medical guidewire of claim 15, wherein the magnetically responsive element is made of neodymium-iron-boron.

17. The magnetically navigable medical guidewire of claim 15, wherein the magnetically responsive element is made of a material of high magnetic permeability.

18. The magnetically navigable medical guidewire of claim 10, wherein the magnetically responsive element is responsively oriented in a selected direction by a magnetic navigation system through the interaction of magnetic fields associated with the magnetic member and at least one external source magnet outside the subject body.

19. The magnetically navigable medical guidewire of claim 18, wherein the tip of the guidewire is capable of being deflected a minimum of 30 degrees over a length of 1 cm measured proximally from the tip when subjected to a suitably oriented magnetic field of magnitude at least 0.06 Tesla.

20. A magnetically navigable medical guidewire, comprising:
    an elongate wire having a proximal end, and a distal end;
    a cylindrical member disposed on the distal end of the elongate wire, wherein the cylindrical member has a hollow section and a threaded end comprising an external helical thread on the outer surface of the distal end of the elongate wire forming at least one complete thread turn over a predetermined thread length; and
    a magnetically responsive element disposed within the hollow section of the cylindrical member, wherein the magnetically responsive element is of a size and shape sufficient to cause the distal end of the guide wire to stay aligned with the direction of a magnetic field while a torque is applied to the guide wire to rotate the guide wire, such that the distal tip rotates while maintaining its alignment with the field.

21. The magnetically navigable medical guidewire of claim 20, wherein the magnetically responsive element is encapsulated within the hollow section of the cylindrical member.

22. The magnetically navigable medical guidewire of claim 20, wherein the threaded end comprises a number of complete helical thread turns in the range of one to ten complete turns over a predetermined length of 0.5 to 4.0 millimeters.

23. The magnetically navigable medical guidewire of claim 22, wherein the threaded end preferably comprises three to four complete helical thread turns over a predetermined length of about 2.2 millimeters.

24. The magnetically navigable medical guidewire of claim 23, wherein the cylindrical member is made of gold or a gold alloy.

25. The magnetically navigable medical guidewire of claim 20, wherein the magnetically responsive element has a length in the range of 1 to 5 millimeters.

26. The magnetically navigable medical guidewire of claim 25, wherein the magnetically responsive element is made of neodymium-iron-boron.

27. The magnetically navigable medical guidewire of claim 25, wherein the magnetically responsive element is made of a material of high magnetic permeability.

28. The magnetically navigable medical guidewire of claim 20, wherein the magnetically responsive element is responsively oriented in a selected direction by a magnetic navigation system through the interaction of magnetic fields associated with the magnetic member and at least one external source magnet outside the subject body.

29. The magnetically navigable medical guidewire of claim 28, wherein the tip of the guidewire is capable of being deflected a minimum of 30 degrees over a length of 1 cm measured proximally from the tip when subjected to a suitably oriented magnetic field of magnitude at least 0.06 Tesla.

30. A magnetically navigable medical guidewire, comprising:
an elongate wire having a proximal end, and a distal end;
at least one magnetically responsive element disposed on the distal end of the elongate wire, wherein the magnetically responsive element is of a size and shape sufficient to cause the distal end of the guide wire to stay aligned with the direction of a magnetic field while a torque is applied to the guide wire to rotate the guide wire, such that the distal tip rotates while maintaining its alignment with the field; and
a threaded tip section located at the distal end of the guidewire, wherein the threaded tip comprises an external helical thread on the outer surface of the distal end of the elongate wire forming at least one complete thread turn over a predetermined thread length.

31. The magnetically navigable medical guidewire of claim 30, further comprising a flexible tube disposed over the elongate wire, at least one magnetically responsive element, and a portion of the threaded tip section to provide a seal around the elongate wire and at least one magnetically responsive element.

32. The magnetically navigable medical guidewire of claim 30, wherein the threaded end comprises a number of complete helical thread turns in the range of one to ten complete turns over a predetermined length of 0.5 to 4.0 millimeters.

33. The magnetically navigable medical guidewire of claim 32, wherein the threaded end preferably comprises three to four complete helical thread turns over a predetermined length of about 2.2 millimeters.

34. The magnetically navigable medical guidewire of claim 30, wherein the at least one magnetically responsive element has a length in the range of 0.5 to 5 millimeters.

35. The magnetically navigable medical guidewire of claim 34, wherein the at least one magnetically responsive element is made of neodymium-iron-boron.

36. The magnetically navigable medical guidewire of claim 34, wherein the at least one magnetically responsive element is made of a material of high magnetic permeability.

37. The magnetically navigable medical guidewire of claim 30, wherein the at least one magnetically responsive element is responsively oriented in a selected direction by a magnetic navigation system through the interaction of magnetic fields associated with the magnetic member and at least one external source magnet outside the subject body.

38. The magnetically navigable medical guidewire of claim 37, wherein the tip of the guidewire is capable of being deflected a minimum of 30 degrees over a length of 1 cm measured proximally from the tip when subjected to a suitably oriented magnetic field of magnitude at least 0.06 Tesla.

39. The magnetically navigable medical guidewire of claim 30, wherein the tip of the guidewire further comprises a tapered pointed tip leading into the external helical thread.

* * * * *